US009778557B2

(12) United States Patent
Eldar et al.

(10) Patent No.: US 9,778,557 B2
(45) Date of Patent: Oct. 3, 2017

(54) FREQUENCY-DOMAIN BEAMFORMING (71) Applicant: Technion Research & Development Foundation Ltd., Haifa (IL)

(72) Inventors: Yonina Eldar, Haifa (IL); Tatiana Chernyakova, Haifa (IL); Ron Amit, Herzliya (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 573 days.

(21) Appl. No.: 14/097,281

(22) Filed: Dec. 5, 2013

(65) Prior Publication Data

US 2014/0160883 A1    Jun. 12, 2014

Related U.S. Application Data

(60) Provisional application No. 61/733,913, filed on Dec. 6, 2012.

(51) Int. Cl.
| | |
|---|---|
| *G01S 7/52* | (2006.01) |
| *G03B 42/06* | (2006.01) |
| *A61B 8/08* | (2006.01) |
| *G10K 11/34* | (2006.01) |
| *G01S 7/32* | (2006.01) |

(52) U.S. Cl.
CPC ............... *G03B 42/06* (2013.01); *A61B 8/52* (2013.01); *G01S 7/52025* (2013.01); *G10K 11/343* (2013.01); *G01S 7/32* (2013.01)

(58) Field of Classification Search
CPC ...... G01S 7/32; G01S 7/52025; G10K 11/343
See application file for complete search history.

(56) References Cited

U.S. PATENT DOCUMENTS

| | | | | |
|---|---|---|---|---|
| 4,112,430 A | * | 9/1978 | Ladstatter ................. | G01S 3/48 |
| | | | | 342/196 |
| 2001/0034481 A1 | * | 10/2001 | Horn ........................ | A61B 7/00 |
| | | | | 600/407 |

(Continued)

FOREIGN PATENT DOCUMENTS

GB        2329072 A        3/1999

OTHER PUBLICATIONS

Wagner, Compressed Beamforming in Ultrasound Imaging, http://arxiv.org/pdf/1202.6037.pdf, Apr. 10, 2012, pp. 1-14.*

(Continued)

*Primary Examiner* — Hovhannes Baghdasaryan
(74) *Attorney, Agent, or Firm* — D. Kligler I.P. Services Ltd.

(57) ABSTRACT

A method includes receiving from multiple transducers respective signals including reflections of a transmitted signal from a target. An image of the target is produced irrespective of sparsity of the received signals, by computing transducer-specific frequency-domain coefficients for each of the received signals, deriving, from the transducer-specific frequency-domain coefficients, beamforming frequency-domain coefficients of a beamformed signal in which the reflections received from a selected direction relative to the transducers are emphasized, and reconstructing the image of the target at the selected direction based on the beamforming frequency-domain coefficients.

24 Claims, 3 Drawing Sheets

(56) References Cited

U.S. PATENT DOCUMENTS

| | | | |
|---|---|---|---|
| 2011/0222791 A1* | 9/2011 | Mansour | G01S 7/52034 |
| | | | 382/240 |
| 2011/0225218 A1 | 9/2011 | Eldar et al. | |
| 2011/0270086 A1* | 11/2011 | Hoctor | A61B 8/4488 |
| | | | 600/443 |
| 2013/0038479 A1 | 2/2013 | Eldar et al. | |

OTHER PUBLICATIONS

Candes et al., "Compressed Sensing with Coherent and Redundant Dictionaries", Applied and Computational Harmonic Analysis, vol. 31, No. 1, pp. 59-73, year 2011.
Tur et al., "Innovation Rate Sampling of Pulse Streams with Application to Ultrasound Imaging", IEEE Transactions on Signal Processing, vol. 59, No. 4, pp. 1827-1842, Jan. 5, 2011.
Steinberg, B., "Digital Beamforming in Ultrasound," IEEE Transactions on Ultrasonics, Ferroelectrics and Frequency Control, vol. 39, No. 6, pp. 716-721, Nov. 1992.
Gedalyahu et al., "Multichannel Sampling of Pulse Streams at the Rate of Innovation," IEEE Transactions on Signal Processing, vol. 59, No. 4, pp. 1491-1504, Jan. 4, 2011.
Baransky et al., "A Sub-Nyquist Radar Prototype: Hardware and Algorithms", Department of Electrical Engineering, Technion-Israel Institute of Technology, pp. 1-12, Jul. 6, 2013.
Candes et al., "I1-magic: Recovery of Sparse Signals via Convex Programming," 19 pages, Oct. 2005.
Grant et al., "CVX: Matlab software for disciplined convex programming," 56 pages, year 2008.
Beck et al., "A Fast Iterative Shrinkage-Thresholding Algorithm for Linear Inverse Problems," SIAM Journal on Imaging Sciences, vol. 2, No. 1, pp. 183-202, year 2009.
Hale et al., "A Fixed-Point Continuation Method for 11-Regularized Minimization with Application to Compressed Sensing", CAAM Technical Report TR07-07, Rice University, pp. 1-45, Jul. 7, 2007.
Shannon,C., "Communication in the Presence of Noise", Proceedings of the IEEE, vol. 86, No. 2, pp. 447-457, Feb. 1998 (re-printed from Proceedings of the IRE, vol. 37, No. 1, pp. 10-21, 1949).
Szabo, T., "Diagnostic Ultrasound Imaging: Inside Out", Academic press, pp. 1-571, year 2004.
Vetterli et al., "Sampling signals with finite rate of innovation", IEEE Transactions on Signal Processing, vol. 50, No. 6, pp. 1417-1428, year 2002.
Jensen, J., "Linear description of ultrasound imaging systems", Notes for the International Summer School on Advanced Ultrasound Imaging Technical University of Denmark, vol. 5, pp. 1-71, Release 1.01, Jun. 29, 2001.
Kutyniok et al., "Compressed Sensing: Theory and Applications", Cambridge University Press, vol. 20, pp. 1-22, Mar. 2012.
Tropp et al., "Signal Recovery From Random Measurements Via Orthogonal Matching Pursuit", IEEE Transactions on Information Theory, vol. 53, No. 12, pp. 4655-4666, Dec. 2007.
Michaeli et al., "Xampling at the Rate of Innovation", IEEE Transactions on Signal Processing, No. 99, pp. 1121-1131, Nov. 23, 2011.
Mishali et al., "Xampling: Signal Acquisition and Processing in Union of Subspaces", IEEE Transactions on Signal Processing, vol. 59, No. 10, pp. 4719-4734, Mar. 8, 2011.
Mishali et al., "Xampling: Analog to Digital at Sub Nyquist Rates", Technion—Israel Institute of Technology, Department of Electrical Engineering, 16 pages, Dec. 13, 2009.
Becker et al.,"NESTA: A Fast and Accurate First-Order Method for Sparse Recovery", SIAM Journal on Imaging Sciences, vol. 4, No. 1, pp. 1-39, year 2011.
O'Donnell et al., "Real-Time Phased Array Imaging Using Digital Beam Forming and Autonomous Channel Control", Proceedings of the IEEE 1990 Ultrasonics Symposium, pp. 1499-1502, Dec. 4-7, 1990.
Trees et al., "Optimum Array Processing: Part IV of Detection, Estimation, and Modulation Theory", Willy-Interscience, 32 pages, year 2004.
Oppenheim et al., "Discrete-time signal processing", Second Edition, vol. 5, Prentice hall Upper Saddle River, 897 pages ,year 1999.
Eilam et al., "Sub-nyquist 6 medical ultrasound imaging: En route to cloud processing", IEEE GlobalSip 2013, pp. 1017-1020, Dec. 3-5, 2013.
Wang et al., "Image Quality Assessment: From Error Visibility to Structural Similarity", IEEE Transactions on Image Processing, vol. 13, No. 4, 14 pages, Apr. 2004.
Sarkar et al., "Using the Matrix Pencil Method to Estimate the Parameters of a Sum of Complex Exponentials", IEEE Antennas and Propagation Magazine, vol. 37, No. 1, Feb. 1995.
Stoica et al., "Introduction to Spectral Analysis", vol. 89, Prentice Hall ,Upper Saddle River, 6 pages, year 1997.
Rudelson et al., "On Sparse Reconstruction from Fourier and Gaussian Measurements", Communications on Pure and Applied Mathematics, vol. LXI, pp. 1025-1045, year 2008.
Notomi et al., "Measurement of Ventricular Torsion by Two-Dimensional Ultrasound Speckle Tracking Imaging", Journal of the American College of Cardiology, vol. 45, No. 12, pp. 2034-2041, year 2005.
Suffoletto et al., "Images to Quantify Dyssynchrony and Predict Response to Cardiac Resynchronization Novel Speckle-Tracking Radial Strain From Routine Black-and-White Echocardiographic Therapy", Circulation, vol. 113, No. 7, pp. 960-968, year 2006.
Nesterov, Y., "Smooth minimization of non-smooth functions" Mathematical Programming, vol. 103, No. 1, 26 pages, Jan. 10, 2003.
The CVX Users' Guide, Release 2.0 (beta), CVX Research, Inc, 100 pages, Nov. 19, 2013.
Duarte et al., "Structured Compressed Sensing: From Theory to Applications", IEEE Transactions on signal processing, vol. 59, No. 9, pp. 4053-4085, Sep. 1, 2011.
European Patent Application # 13195572.6 Search Report dated Mar. 4, 2014.
Chernyakova et al., "Fourier Domain Beamforming:The Path to Compressed Ultrasound Imaging", pp. 1-11, Jul. 24, 2013.
Chernyakova et al., "Fourier Domain Beamforming for medical Ultrasound", 2013 IEEE international conference on acoustics, speech and signal processing, pp. 924-928, Dec. 20, 2012.
Wagner et al., "Compressed Beamforming in Ultrasound Imaging", IEEE Transactions on signal processing, vol. 60, No. 9, pp. 4643-4657, Sep. 1, 2012.
Wagner et al., "Xampling in Ultrasound Imaging", Medical Imaging 2011: Ultrasonic imaging, Tomography, and Therapy, vol. 7968, No. 1, pp. 1-17, Mar. 3, 2011.
Chernyakova et al., "Fourier-Domain Beamforming: The Path to Compressed Ultrasound Imaging", IEEE Transactions on Ultrasonics, Ferroelectrics and Frequency Control ,vol. 61, No. 8, pp. 1252-1267, Aug. 2014.
Duarte et al., "Structured Compressed Sensing: From Theory to Applications", IEEE, 60 pages, Jul. 28, 2011.
CN Application # 201310657146.9 Office Action dated Sep. 20, 2016.
EP Application # 13195572.6 Office Action dated Oct. 10, 2016.

* cited by examiner

FREQUENCY-DOMAIN BEAMFORMING

CROSS-REFERENCE TO RELATED APPLICATIONS

This application claims the benefit of U.S. Provisional Patent Application 61/733,913, filed Dec. 6, 2012, whose disclosure is incorporated herein by reference.

FIELD OF THE INVENTION

The present invention relates generally to signal processing, and particularly to methods and systems for frequency-domain beamforming.

BACKGROUND OF THE INVENTION

Beamforming is a spatial filtering technique that is used in a wide variety of fields and applications, such as wireless communication, ultrasound imaging and other medical imaging modalities, radar, sonar, radio-astronomy and seismology, among others. Beamforming techniques for ultrasound imaging are described, for example, by Steinberg, in "Digital Beamforming in Ultrasound," IEEE Transactions on Ultrasonics, Ferroelectrics and Frequency Control, volume 39, number 6, 1992, pages 716-721, which is incorporated herein by reference.

Tur et al. describe efficient ultrasound signal sampling techniques, in "Innovation Rate Sampling of Pulse Streams with Application to Ultrasound Imaging," IEEE Transactions on Signal Processing, volume 59, number 4, 2011, pages 1827-1842, which is incorporated herein by reference. Wagner et al. describe beamforming techniques applied to sub-Nyquist samples of received ultrasound signals, in "Compressed Beamforming in Ultrasound Imaging," IEEE Transactions on Signal Processing, volume 60, number 9, September, 2012, pages 4643-4657, which is incorporated herein by reference.

SUMMARY OF THE INVENTION

An embodiment of the present invention that is described herein provides a method including receiving from multiple transducers respective signals including reflections of a transmitted signal from a target. An image of the target is produced irrespective of sparsity of the received signals, by computing transducer-specific frequency-domain coefficients for each of the received signals, deriving, from the transducer-specific frequency-domain coefficients, beamforming frequency-domain coefficients of a beamformed signal, in which the reflections received from a selected direction relative to the transducers are emphasized, and reconstructing the image of the target at the selected direction based on the beamforming frequency-domain coefficients.

In some embodiments, deriving the beamforming frequency-domain coefficients includes computing the beamforming frequency-domain coefficients only within an effective bandwidth of the beamformed signal. In an embodiment, reconstructing the image includes applying an inverse Fourier transform to the beamforming frequency-domain coefficients. In another embodiment, deriving the beamforming frequency-domain coefficients includes computing the beamforming frequency-domain coefficients only within a partial sub-band within an effective bandwidth of the beamformed signal.

In a disclosed embodiment, reconstructing the image includes applying a Compressed sensing (CS) or sparse recovery process to the beamformed frequency-domain coefficients. In another embodiment, reconstructing the image includes applying to the beamformed frequency-domain coefficients an algorithm for extracting sinusoids from a sum of sinusoids. In yet another embodiment, reconstructing the image includes estimating the beamformed signal in time-domain based on the beamforming frequency-domain coefficients, and reconstructing the image from the estimated beamformed signal. In an example embodiment, estimating the beamformed signal includes applying an l1-norm optimization to the beamforming frequency-domain coefficients.

In some embodiments, deriving the beamforming frequency-domain coefficients includes computing a weighted average of the transducer-specific frequency-domain coefficients. Computing the weighted average may include applying to the transducer-specific frequency-domain coefficients predefined weights that are independent of the received signals. In an embodiment, reconstructing the image of the target includes reconstructing both dominant reflections and speckle based on the beamforming frequency-domain coefficients. In an embodiment, computing the transducer-specific frequency-domain coefficients includes deriving the transducer-specific frequency-domain coefficients from sub-Nyquist samples of the received signals.

There is additionally provided, in accordance with an embodiment of the present invention, apparatus including an input interface and processing circuitry. The input interface is configured to receive from multiple transducers respective signals including reflections of a transmitted signal from a target. The processing circuitry is configured to produce an image of the target irrespective of sparsity of the received signals, by computing transducer-specific frequency-domain coefficients for each of the received signals, deriving, from the transducer-specific frequency-domain coefficients, beamforming frequency-domain coefficients of a beamformed signal in which the reflections received from a selected direction relative to the transducers are emphasized, and reconstructing the image of the target at the selected direction based on the beamforming frequency-domain coefficients.

There is also provided, in accordance with an embodiment of the present invention, a method including receiving from multiple transducers respective signals comprising reflections of a transmitted signal from a target. Transducer-specific frequency-domain coefficients are computed for each of the received signals. Beamforming frequency-domain coefficients of a beamformed signal, in which the reflections received from a selected direction relative to the transducers are emphasized, are derived from the transducer-specific frequency-domain coefficients. An image of the target at the selected direction is reconstructed based on the beamforming frequency-domain coefficients, under a constraint that the received signals are compressible.

There is further provided, in accordance with an embodiment of the present invention, apparatus including an input interface and processing circuitry. The input interface is configured to receive from multiple transducers respective signals including reflections of a transmitted signal from a target. The processing circuitry is configured to compute transducer-specific frequency-domain coefficients for each of the received signals, to derive, from the transducer-specific frequency-domain coefficients, beamforming frequency-domain coefficients of a beamformed signal, in which the reflections received from a selected direction relative to the transducers are emphasized, and to reconstruct an image of the target at the selected direction based on the beamforming frequency-domain coefficients, under a constraint that the received signals are compressible.

The present invention will be more fully understood from the following detailed description of the embodiments thereof, taken together with the drawings in which:

DETAILED DESCRIPTION OF EMBODIMENTS

Overview

Embodiments of the present invention that are described herein provide improved methods and system for beamforming of received signals. Although the embodiments described herein refer mainly to beamforming in the context of ultrasound imaging, the disclosed techniques can be used in various other suitable applications that involve beamforming, such as other medical imaging modalities, wireless communication, radar, sonar, speech and other audio processing, radio-astronomy and seismology.

An ultrasound imaging system typically transmits ultrasound signals into target tissue using an array of ultrasound transducers, and then receives and processes the signals reflected from the tissue. Receive-side beamforming in such a system generally involves summing the received signal after delaying each signal by an appropriate delay, such that all the reflections from a desired direction and range align in time. This process is typically repeated over multiple directions and ranges, so as to construct an ultrasound image that covers a sector of interest. Performing the receive-side beamforming computations in the time domain requires very high sampling rates and high computational complexity.

In some disclosed embodiments, an ultrasound imaging system performs receive-side beamforming in the frequency domain rather than in the time domain. The system computes Fourier coefficients for the signal received via each transducer, and then derives the Fourier coefficients of the beamformed signal directly from the Fourier coefficients of the received signals. Only at this stage, the system reconstructs the time-domain beamformed signal from its Fourier coefficients.

In some embodiments, the system derives the Fourier coefficients of the beamformed signal by calculating a weighted sum of the Fourier coefficients of the received signals. The weights used in the summation are signal-independent, and can therefore be pre-calculated off-line. Since the weighting function decays rapidly, in most cases it is sufficiently accurate to sum over a small number of Fourier coefficients.

Performing the beamforming operation in the frequency domain enables the system to use a very low sampling rate, while still producing high-quality images. In some embodiments, the Fourier coefficients are computed only within the effective bandwidth of the ultrasound signal, and therefore can be derived from low-rate samples of the received signals. Further reduction in sampling rate is achievable by computing the Fourier coefficients for only a portion of the signal bandwidth.

In some embodiments, the system performs beamforming and reconstruction without assuming that the signal is sparse or that the signal has a Finite Rate of Innovation (FRI). In other embodiments, the system exploits the structure of the signal, e.g., by using the FRI nature of the signal or the fact that the signal has a small number of strong reflectors. Reconstruction in these embodiments can be performed, for example, by using sparse recovery methods such as l1-norm optimization or various other recovery algorithms. Regardless of whether signal structure is relied upon or not, the disclosed techniques perform beamforming in the frequency domain, and then perform recovery from either a partial or full bandwidth, either using linear operations based on inverse FFT and related weighting methods, or by using sparse recovery techniques.

A major advantage of the disclosed techniques is the ability to perform beamforming in the frequency domain at low sampling and processing rates. When the full signal bandwidth is used, the proposed technique uses considerably lower sampling and processing rates than conventional time-domain processing, and provides equivalent imaging performance. Even when the sampling and processing rates are further reduced by using only partial bandwidth, the proposed technique is able to image both strong reflections and speckle with high quality, which is highly important in various diagnostic applications. Example simulation results, which demonstrate the performance of the disclosed techniques, are given and discussed in U.S. Provisional Patent Application 61/733,913, cited above.

System Description

Figure 1:
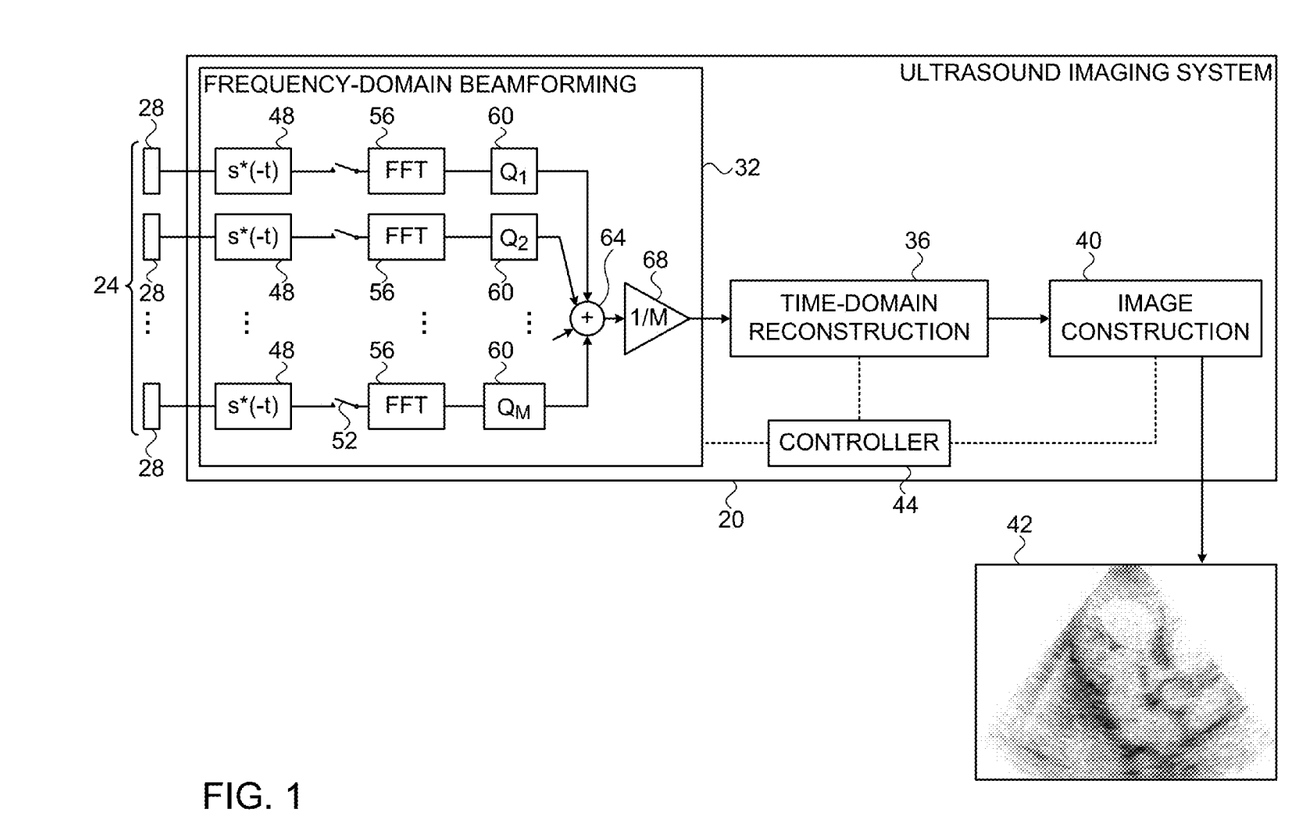
FIG. 1 is a block diagram that schematically illustrates an ultrasound imaging system, in accordance with an embodiment of the present invention.

FIG. 1 is a block diagram that schematically illustrates an ultrasound imaging system 20, in accordance with an embodiment of the present invention. System 20 is typically used for producing ultrasound images of a target organ of a patient.

System 20 comprises an array 24 of ultrasound transducers 28, which are coupled to the patient body during imaging. The transducers transmit an ultrasonic signal into the tissue, and receive respective signals that comprise reflections ("echoes") of the transmitted signal from the tissue. The received signals are processed, using methods that are described herein, so as to reconstruct and display an ultrasound image 42 of the target organ.

In the embodiment of FIG. 1, system 20 comprises a frequency-domain beamforming unit 32, a time-domain reconstruction unit 36 and an image construction unit 40. A controller 44 controls the various system components. Beamforming unit 32 computes, for each transducer 28, a set of Fourier coefficients of the signal received by that transducer. These coefficients are referred to as transducer-specific Fourier coefficients. Unit 32 then combines the transducer-specific Fourier coefficients to produce a set of Fourier coefficients that represent a directional beamformed signal, which is produced from the multiple signals received by transducers 28. In the beamformed signal, the reflections from a selected direction in the tissue relative to array 24 are emphasized. The Fourier coefficients of the beamformed signal are referred to as beamforming Fourier coefficients.

Unit 32 derives the beamforming Fourier coefficients from the transducer-specific Fourier coefficients directly in the frequency domain. The beamforming Fourier coefficients are provided as input to time-domain reconstruction unit 36. Unit 36 reconstructs the beamformed signal for the selected direction from the beamforming Fourier coefficients.

The process of frequency-domain beamforming and time-domain reconstruction is typically repeated for multiple angular directions relative to array 24, e.g., over a desired angular sector. Image construction unit 40 constructs a graphical image of the tissue in the scanned sector, e.g., image 42 shown in the figure. The resulting image is provided as output, e.g., displayed to an operator and/or recorded.

In the present embodiment, beamforming unit 32 comprises multiple processing chains, a respective processing chain per each transducer 28. Each processing chain comprises a filter 48, a sampler 52, a Fast Fourier Transform (FFT) module 56 and a weighting module 60. The outputs of the processing chains are summed by an adder 64, and the sum is normalized by a gain module 68. (The configuration of the processing chains in unit 32 is an example configuration. In alternative embodiments, the processing chains may use other elements or configurations for computing the Fourier coefficients of the received signals.) The output of module 68 comprises the beamforming Fourier coefficients, i.e., the Fourier coefficients of the beamformed signal. The operation of unit 32 is described in detail below.

The system configuration of FIG. 1 is an example configuration, which is chosen purely for the sake of conceptual clarity. In alternative embodiments, any other suitable system configuration can be used. The elements of system 20 may be implemented using hardware. Digital elements can be implemented, for example, in one or more off-the-shelf devices, Application-Specific Integrated Circuits (ASICs) or FPGAs. Analog elements can be implemented, for example, using discrete components and/or one or more analog ICs. Some system elements may be implemented, additionally or alternatively, using software running on a suitable processor, e.g., a Digital Signal Processor (DSP). Some system elements may be implemented using a combination of hardware and software elements.

In some embodiments, some or all of the functions of system 20 may be implemented using a general-purpose computer, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

System elements that are not mandatory for understanding of the disclosed techniques, such as circuitry relating to transmission of the ultrasound signal, have been omitted from the figure for the sake of clarity. An alternative example implementation is described in FIG. 4 further below.

Figure 4:
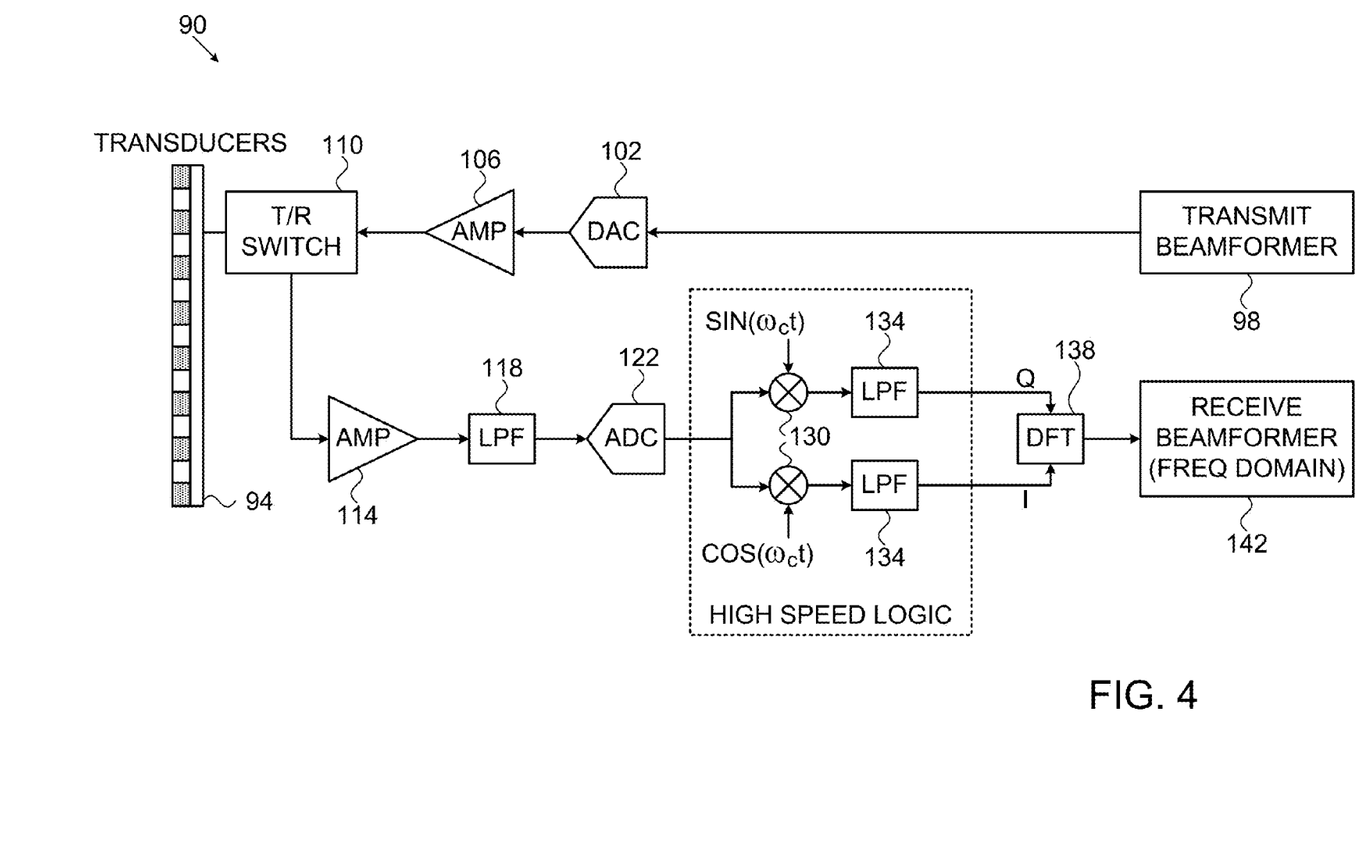
FIG. 4 is a block diagram that schematically illustrates an ultrasound imaging system, in accordance with another embodiment of the present invention.

The various processing elements of system 20, e.g., units 32, 36 and 40, are sometimes referred to collectively as processing circuitry that carries out the disclosed techniques. Such processing circuitry typically operates in conjunction with a front end or other input interface that receives the signals from the ultrasound transducers. The front end (or input interface) is not shown in FIG. 1 for the sake of clarity, but is shown in FIG. 4 below.

The description that follows refers mainly to Fourier coefficients. Generally, however, the disclosed techniques can be carried out using coefficients of any suitable frequency-domain transform or signal representation, such as, for example, Fourier coefficients, Fast Fourier Transform (FFT) coefficients and Discrete Fourier Transform (DFT) coefficients. In the context of the present patent application and in the claims, all these types of coefficients are referred to as "frequency-domain coefficients."

Time-Domain Beamforming

Figure 2:
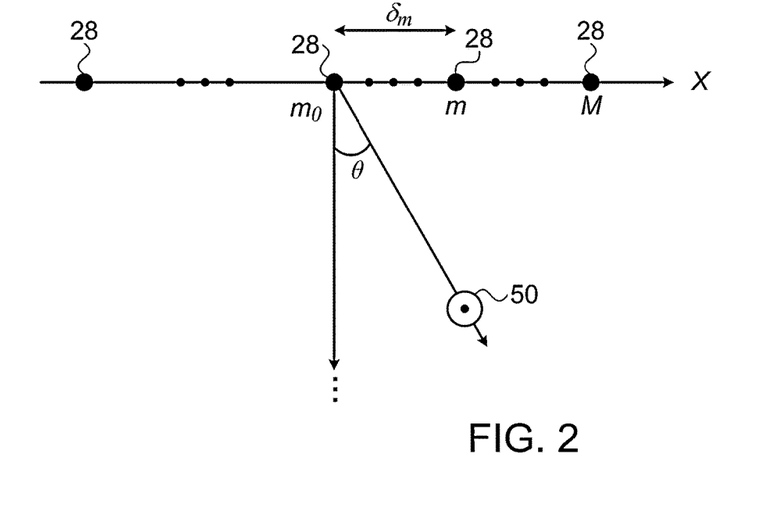
FIG. 2 is a diagram showing the geometry of an array of ultrasound transducers, in accordance with an embodiment of the present invention.

FIG. 2 is a diagram showing the geometry of array 24 of ultrasound transducers 28, in accordance with an embodiment of the present invention. The number of transducers in the array is denoted M, the transducers are assumed to lie in a linear array along the x axis with a reference element denoted $m_0$ at the origin. The model assumed herein is planar, with the perpendicular axis to the x axis denoted z. The distance between the $m^{th}$ transducer and the origin is denoted $\delta_m$. This array geometry is given purely by way of example. The disclosed techniques can be used with any other suitable array geometry, including, for example, two-dimensional transducer arrays used for three-dimensional imaging.

The imaging cycle for a particular angle θ begins at time t=0, at which the ultrasound signal is transmitted from the array to the tissue. The signal is reflected from a point reflector 50 located at a certain distance from the array at direction θ. Reflector 50 scatters the signal, and the scattered echoes are eventually received by the M transducers 28 at times that depend on their distances from the reflector.

Let $\phi_m(t; \theta)$ denote the signal received by the $m^{th}$ transducer, and let $\hat{\tau}_m(t; \theta)$ denote the time of reception of the echo at the $m^{th}$ transducer. The beamforming operation involves applying appropriate time delays to the signals received by the different transducers, such that the echoes become time-aligned, and averaging the delayed signals. The time delays depend on the geometry of the array, on the direction θ, and on the distance to reflector 50 along direction θ.

The delayed, and thus time-aligned, signal of the $m^{th}$ transducer is given by $$\hat{\varphi}_m(t; \theta) \quad [1]$$

$$\tau_m(t; \theta) = \frac{1}{2}\left(t + \sqrt{t^2 - 4(\delta_m/c)t \cdot \sin\theta + 4(\delta_m/c)^2}\right) \quad [2]$$

wherein c denotes the propagation velocity of the signal in the tissue. The beamformed signal is given by $$\Phi(t; \theta) = \frac{1}{M}\sum_{m=1}^{M} \hat{\varphi}_m(t; \theta) \quad [3]$$

It is important to note that the beamformed signal is both directed toward direction θ, and focused on the specific distance of reflector 50 from the array. This kind of beamforming (sometimes referred to as "dynamic focusing") provides high Signal-to-Noise Ratio (SNR) and fine angular resolution, but on the other hand incurs heavy computational load and high sampling rate. The beamforming scheme described above is typical of ultrasound applications, and is chosen purely by way of example. In alternative embodiments, the disclosed techniques can be used with any other suitable beamforming scheme.

Frequency-Domain Beamforming

In some embodiments, system 20 performs the beamforming operation in the frequency domain rather than in the time domain. As a result, sampling rate requirements and processing rates can be relaxed considerably. The disclosed techniques perform frequency-domain beamforming without making any assumptions (e.g., sparsity) on the properties of the received signals. When such information regarding the signal properties is available, beamforming in frequency can be used to further reduce the rate.

The following description shows the relation between the Fourier coefficients of the individual signals received by the various transducers (denoted transducer-specific Fourier coefficients) and the Fourier coefficients of the beamformed signal (denoted beamforming Fourier coefficients). The description that follows refers to the specific beamforming scheme of Equations [1] and [2]. The disclosed techniques are applicable in a similar manner to other forms of beamforming.

The support of the beamformed signal $\Phi(t; \theta)$ is the finite time interval $[0, T_B(\theta))$, wherein $T_B(\theta) < T$, with T denoting the penetration depth of the tissue in question. The Fourier coefficients of $\Phi(t; \theta)$ with respect to interval $[0, T)$ are given by $$c_k^s = \frac{1}{T} \int_0^T I_{[0, T_B(\theta))}(t) \Phi(t; \theta) e^{-i\frac{2\pi}{T}kt} dt \quad [4]$$

wherein $I_{[a,b)}$ denotes an indicator function that is equal to unity for $a \le t < b$ and zero otherwise. The beamforming Fourier coefficients can therefore be written as $$c_k^s = \frac{1}{M} \sum_{m=1}^{M} c_{k,m}^s \quad [5]$$

wherein $c_{k,m}^s$ are defined as $$c_{k,m}^s = \frac{1}{T} \int_0^T g_{k,m}(t; \theta) \varphi_m(t; \theta) dt \quad [6]$$

with $$g_{k,m}(t; \theta) = q_{k,m}(t; \theta) e^{-i\frac{2\pi}{T}kt}, \quad [7]$$

$$q_{k,m}(t; \theta) = I_{[|\gamma_m|, \tau_m(T;\theta))}(t) \left(1 + \frac{\gamma_m^2 \cos\theta^2}{(t - \gamma_m \sin\theta)^2}\right) \times \quad [8]$$
$$\exp\left\{i\frac{2\pi}{T} k \frac{\gamma_m - t\sin\theta}{t - \gamma_m \sin\theta} \gamma_m\right\} \gamma_m$$
$$= \delta_m / c$$

Denoting the $n^{th}$ Fourier coefficient by $\phi_m^s[n]$, Equation [6] can be written as $$c_{k,m}^s = \sum_n \varphi_m^s[k-n] Q_{k,m,\theta}[n] \quad [9]$$

wherein $Q_{k,m,\theta}[n]$ are the Fourier coefficients of the distortion function $q_{k,m}(t; \theta)$ with respect to $[0, T)$.

In practice, $c_{k,m}^s$ can be well approximated by replacing the infinite sum in Equation [9] with a finite sum:

$$c_{k,m}^s \cong \sum_{n \in v(k)} \varphi_m^s[k-n] Q_{k,m,\theta}[n] \quad [10]$$

The set v(k) depends on the decay properties of $\{Q_{k,m,\theta}[n]\}$. Numerical analysis of this function shows that most of the energy of the set $\{Q_{k,m,\theta}[n]\}$ is concentrated around the DC component, and therefore it makes sense to select $v(k) = \{-N_1, \ldots, N_2\}$:

$$c_{k,m}^s \cong \sum_{n=-N_1}^{N_2} \varphi_m^s[k-n] Q_{k,m,\theta}[n] \quad [11]$$

In most practical cases, taking the finite sum over the twenty most significant elements in $\{Q_{k,m,\theta}[n]\}$ provides a sufficiently-accurate approximation. Alternatively, however, other finite ranges and/or other approximations can also be used.

Let $\beta$, $|\beta|=B$ denote the set of transducer-specific Fourier coefficients corresponding to the actual signal bandwidth, i.e., the values of k for which $\phi_m^s[k]$ is non-zero or at least larger than a threshold. It follows that the bandwidth $\beta_{BF}$ of the beamformed signal contains no more than $B+N_1+N_2$ non-zero frequency components.

Computing the elements of $\beta_{BF}$ requires the set $\beta$ for each of the received signals. In a typical imaging scenario, B is on the order of several hundreds of coefficients, while $N_1$ and $N_2$ are no larger than ten. These orders of magnitude imply that $B \gg N_1, N_2$, and thus $B+N_1+N_2 \cong B$. Therefore, the bandwidth of the beamformed signal is approximately the same as the bandwidth of the received signals.

Another result is that in order to calculate an arbitrary subset $\mu \subset \beta_{BF}$ of size M of beamforming Fourier coefficients, no more than $M+N_1+N_2$ transducer-specific Fourier coefficients are needed for each of the received signals $\phi_m(t)$. These properties of frequency-domain beamforming can be used for sampling rate reduction, as will be shown below.

Equations [5] and [11] above define the relationship between the beamforming Fourier coefficients (the Fourier series coefficients of the beamformed signal) and the transducer-specific Fourier coefficients (the Fourier series coefficients of the individual signals received by transducers 28).

A similar relationship can be defined between the DFT coefficients of these signals, sampled at the beamforming rate $f_s$. Let $N = \lfloor T \cdot f_s \rfloor$ denote the resulting number of samples of the beamformed signal. Since $f_s$ is higher than the Nyquist rate of the received signals, the relation between the DFT of length N and the Fourier series coefficients of $\phi_m(t)$ is given by $$\varphi_m^s[n] = \frac{1}{N} \begin{cases} \varphi_m[n], & 0 \le n \le P \\ \varphi_m[N+n], & -P \le n < 0 \\ 0, & \text{otherwise} \end{cases} \quad [12]$$

wherein $\phi_m[n]$ denotes the DFT coefficients and P denotes index of the Fourier transform coefficient corresponding to the highest frequency component.

Equation [12] can be used for substituting Fourier series coefficients $\phi_m^s[n]$ of $\phi_m(t)$ in Equation [11] with DFT coefficients $\phi_m[n]$ of its sampled version. Substituting this result into Equation [5] yields a relationship between the Fourier series coefficients of the beamformed signal and the DFT coefficients of the sampled received signals:

$$c_{k,m}^s \cong \frac{1}{MN} \sum_{m=1}^{M} \sum_{n=-N_1}^{k-\tilde{n}} \varphi_m[k-n]Q_{k,m,\theta}[n] + \sum_{n=k-\tilde{n}+1}^{N_2} \varphi_m[k-n+N]Q_{k,m,\theta}[n] \quad [13]$$

for a properly chosen ñ. Since $f_s$ is higher than the Nyquist rate of the beamformed signal, as well, the DFT coefficients $c_k$ of its sampled version are given by a relationship similar to Equation [12]:

$$c_k = N \begin{cases} c_k^s, & 0 \leq k \leq P \\ c_{k-N}^s, & N-P \leq k < N \\ 0, & \text{otherwise} \end{cases} \quad [14]$$

Equations [13] and [14] thus define the relationship between the DFT coefficients of the beamformed signal and the DFT coefficients of the received signals. As noted above, the above relationship refers to one particular beamforming scheme, which is chosen by way of example. The disclosed techniques are applicable in a similar manner to other forms of beamforming.

This relationship, which is obtained by periodic shift and scaling of Equation [11], retains the properties of the latter. Applying Inverse DFT (IDFT) to the sequence $\{c_k\}_{k=0}^{N-1}$ reconstructs the beamformed signal in the time domain. Reconstruction of the image can be performed by applying image generation operation such as, for example, log-compression and interpolation.

Figure 3:
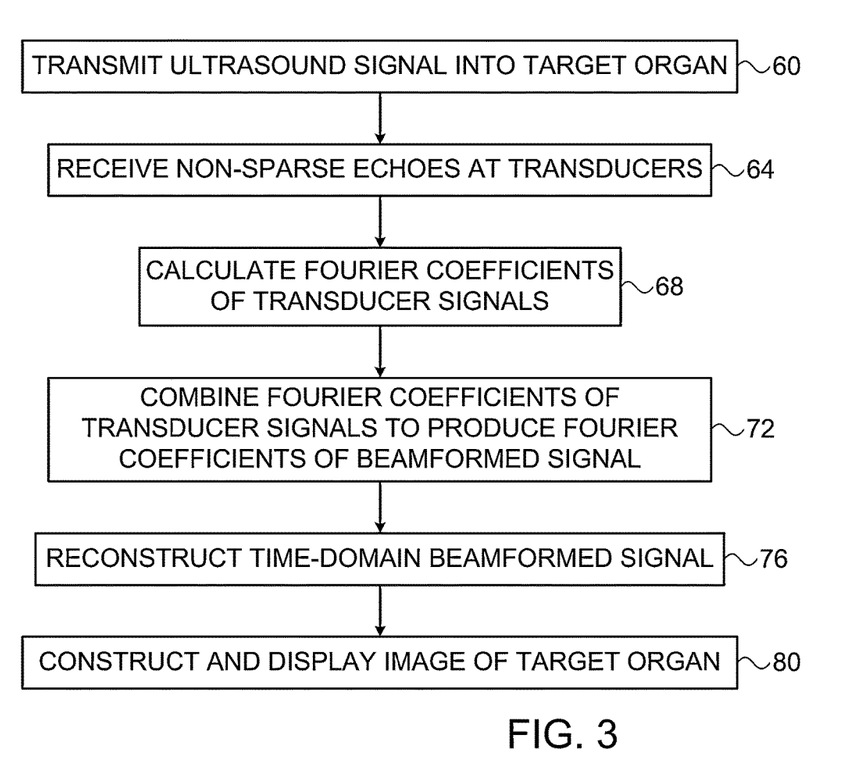
FIG. 3 is a flow chart that schematically illustrates a method for ultrasound imaging, in accordance with an embodiment of the present invention.

FIG. 3 is a flow chart that schematically illustrates a method for ultrasound imaging, performed by system 20 of FIG. 1 above, in accordance with an embodiment of the present invention. The method begins with system 20 transmitting an ultrasound signal into the tissue in question, at a transmission step 60. Transducers 28 receive the reflected echoes, at a reception step 64. Referring to the configuration of FIG. 1, the M processing chains of beamforming unit 32 receive the respective received signals $\{\phi_m(t)\}_{m=1}^{M}$.

Unit 32 computes the transducer-specific Fourier coefficients, at a transducer-specific calculation step 68. In the $m^{th}$ processing chain, filter 48 filters the received signal $\phi_m(t)$ with a suitable kernel $s^*(-t)$. (Filtering with a kernel is one possible example implementation. In alternative embodiments, other suitable analog means can be used, or the signal can first be sampled and then its rate reduced digitally.)

Sampler 52 digitizes the filtered signal at a low sampling rate, which is defined by the effective bandwidth of the transmitted signal, typically corresponding to the Nyquist rate with respect to the effective bandwidth of the transmitted signal. (Sampling at the Nyquist rate is typically used when no signal structure is assumed. When exploiting the signal structure, as will be explained below, only a portion of the signal bandwidth is needed and the sampling rate can be reduced below the Nyquist rate.)

In an embodiment, FFT module 56 computes the DFT coefficients of the digitized signal, to produce $\phi_m[n]$. Weighting module 60 applies weighting with the appropriate elements of $\{Q_{k,m,\theta}[n]\}$. This process is performed in a similar manner in all M processing chains. Alternatively, unit 32 may use any other suitable process to obtain the Fourier coefficients of the signal over the desired bandwidth. The processing and/or sampling rate are affected by this bandwidth only.

Adder 64 of unit 32 sums the weighted transducer-specific Fourier coefficients from the M processing chains, at a combining step 72. The sum is normalized using gain module 68, to produce the beamforming Fourier coefficients. The output of unit 32 is thus $\{c_k\}_{k=0}^{N-1}$.

At a time-domain reconstruction step 76, time-domain reconstruction unit 36 reconstructs the time-domain beamformed signal by applying IDFT to $\{c_k\}_{k=0}^{N-1}$. Alternatively, when signal structure exists, methods that exploit this structure (e.g., sparse recovery techniques) can be used, thereby allowing the use of a smaller number of Fourier coefficients. The process of steps 60-76 is typically repeated over multiple values of θ, e.g., by scanning a desired angular sector relative to array 24. At an image construction step 80, image construction unit 40 constructs and outputs an image of the target organ from the time-domain beamformed signals obtained for the different values of θ.

Example simulation results, which demonstrate the performance of the above-described process, are given and discussed in U.S. Provisional Patent Application 61/733, 913, cited above.

Sampling Rate Reduction

Performing the beamforming operation in the frequency domain enables system 20 to sample the signals received by transducers 28 with a low sampling rate, while still providing high imaging quality.

As explained above, the bandwidth $\beta_{BF}$ of the beamformed signal contains approximately B non-zero frequency components, wherein B denotes the effective bandwidth of the received signals. In some embodiments, unit 32 exploits this property and calculates, for each received signal, the DFT coefficients only for the B non-zero frequency components in $\beta_{BF}$.

The ratio between the cardinality of the set β and the overall number of samples N needed by the conventional beamforming rate $f_s$, depends on the over-sampling factor. The beamforming rate $f_s$ is often defined as four to ten times the pass-band bandwidth of the received signals, meaning B/N is on the order of 0.1-0.25. Assuming it is possible to obtain the set β using B low-rate samples of each received signal, this ratio implies a potential four- to ten-fold reduction in sampling rate relative to time-domain beamforming.

In some embodiments, unit 32 samples the received signals using such a low sampling rate so as to obtain the appropriate non-zero Fourier coefficients. Example sub-Nyquist sampling schemes that can be used for this purpose are described, for example, in the paper "Innovation Rate Sampling of Pulse Streams with Application to Ultrasound Imaging" by Tur et al., in the paper "Compressed Beamforming in Ultrasound Imaging" by Wagner et al., both cited above and incorporated herein by reference, as well as in U.S. Patent Application Publications 2011/0225218 and 2013/0038479, which are both assigned to the assignee of the present patent application and whose disclosures are incorporated herein by reference.

Other suitable sub-Nyquist sampling schemes that can be used by unit 32 are described by Gedalyahu et al., in "Multichannel Sampling of Pulse Streams at the Rate of Innovation," IEEE Transactions on Signal Processing, volume 59, number 4, pages 1491-1504, 2011, which is incorporated herein by reference. Example hardware that can be used for this purpose is described by Baransky et al., in "A Sub-Nyquist Radar Prototype: Hardware and Algorithms," arXiv:1208.2515, August, 2012, which is incorporated herein by reference.

In a sub-Nyquist sampling scheme of this sort, which is implemented by unit 32 in FIG. 1, each received signal is filtered by the respective filter 48 with a kernel s*(−t). The kernel is defined based on the pulse shape of the transmitted ultrasound signal and the set β. After obtaining the set β for each of the received signals (i.e., in each of the processing chains of unit 32), unit 32 calculates the elements of $\beta_{BF}$ using low-rate frequency-domain beamforming as described above.

Reconstruction unit 36 then applies IDFT to the output of unit 32, so as to reconstruct the time-domain beamformed signal. In some embodiments, unit 36 pads the elements of $\beta_{BF}$ with zeros prior to performing IDFT, in order to improve time resolution. In an example implementation intended for comparison with time-domain beamforming, unit 36 pads the elements of $\beta_{BF}$ with N−B zeros. Alternatively, however, any other suitable padding ratio can be used.

In addition to reduction in sampling rate, the above technique reduces the amount of noise in the sampled signal, since conventional time-domain sampling captures noise in the entire frequency spectrum up to the signal frequency and not only within the actual signal bandwidth. Moreover, the above technique reduces processing rates. The effect of this technique on imaging quality is demonstrated in U.S. Provisional Patent Application 61/733,913, cited above.

In some embodiments, unit 32 of system 20 achieves an additional reduction in sampling rate by computing only a partial subset of the non-zero DFT coefficients of the received signals. The subset is denoted μ, $\mu \subset \beta_{BF}$, $|\mu|=M<B_{BF}=|\beta_{BF}|$. In this embodiment, unit 32 computes only $M+N_1+N_2$ frequency components for each received signal, i.e., only $M+N_1+N_2$ samples per processing channel.

When computing only the partial subset μ, in some embodiments unit 36 reconstructs the beamformed signal using Compressed Sensing (CS) techniques or sparse recovery methods. CS-based reconstruction can typically be used when the signal structure is exploited. For example, in some cases it can be assumed that the received signals are sparse and thus can be regarded as having a Finite Rate of Innovation (FRI). Under this assumption, the beamformed signal can be modeled as a sum of replicas of the known transmitted pulse h(t) with unknown amplitudes and delays. See, for example, the article by Wagner at al., cited above. The beamformed signal can thus be written as:

$$\Phi(t; \theta) \cong \sum_{l=1}^{L} \tilde{b}_l h(t - t_l) \quad [15]$$

wherein L denotes the number of scattering elements (reflecting objects) in direction θ, $\{\tilde{b}_l\}_{l=1}^{L}$ denotes the unknown amplitudes of the reflections, and $\{t_l\}_{l=1}^{L}$ denotes the arrival times (delays) of the reflections at the reference transducer $m_0$. Since the pulse shape is known, the beamformed signal is defined in full by the 2L unknown parameters (L amplitudes and L delays). Other sparse models are possible, in which case suitable sparse recovery techniques are typically used. Equation [15] is depicted only as one possible modeling example.

The model of Equation [15] can be rewritten in discrete form, after sampling at the equation at the beamforming rate $f_s$ and quantizing the delays with a quantization step of $1/f_s$, to give:

$$\Phi[n; \theta] \cong \sum_{l=1}^{L} \tilde{b}_l h(t - q_l) \quad [16]$$

$$= \sum_{l=0}^{N-1} b_l h(n - l)$$

wherein $t_l = q_l/f_s$, $N = \lfloor T \cdot f_s \rfloor$, and $$b_l = \begin{cases} \tilde{b}_l & l = q_l \\ 0 & \text{otherwise} \end{cases} \quad [17]$$

Calculating the DFT of both sides of Equation [16] yields the following expression for the DFT coefficients of the beamformed signal:

$$c_k = h_k \sum_{l=0}^{N-1} b_l e^{-i\frac{2\pi}{N}kl} \quad [18]$$

wherein $h_k$ denotes the DFT coefficient of h[n], the transmitted pulse sampled at rate $f_s$. With this notation, recovering $\Phi[n; \theta]$ is equivalent to determining $\{b_l\}_{l=0}^{N-1}$ in Equation [18].

Equivalently, in vector-matrix notation, let c denote a measurement vector of length M whose $k^{th}$ element is $c_k$, $k \in \mu$. Equation [18] can be written as:

$$c = HDb = Ab \quad [19]$$

wherein H is an M-by-M diagonal matrix whose $k^{th}$ diagonal element is $h_k$, D is an M-by-N matrix formed by taking the set μ of rows from an N-by-N DFT matrix, and b is a vector of length N whose $l^{th}$ element is $b_l$. The recovery operation is thus equivalent to determining vector b from vector c.

In some embodiments, reconstruction unit 36 of system 20 determines b by solving the optimization problem:

$$\min_b \|b\|_1 \text{ subject to } \|Ab - c\|_2 \leq \epsilon \quad [20]$$

wherein $\|\ \|_1$ denotes l1 norm (sum of absolute values) and $\|\ \|_2$ denotes l2 norm (Root Mean Square−RMS).

This optimization problem of Equation [20] assumes that the received signals comprise a relatively small number of strong reflectors, plus multiple additional scattered echoes that are typically two orders of magnitude weaker. In other words, vector b is compressible, i.e., approximately but not entirely sparse. This signal model is highly descriptive of ultrasound reflections from tissue, which comprise strong reflections plus a considerable amount of speckle. This property of b is well captured by the l1 norm in Equation [20]. The l1-norm optimization of Equation [20] is one example of a recovery scheme that assumes that the signal is compressible, but not necessarily sparse. In alternative embodiments, any other recovery method that operates under a constraint that the signal is compressible can be used.

Alternatively to the optimization of Equation [20], various other sparse recovery methods can be used, including methods based on l0-norm or other sparse-based techniques. Further alternatively, instead of using sparse recovery methods, unit 36 may use various techniques for recovery of sinusoids from a sum-of-sinusoids. Example methods include MUSIC, ESPRIT, Capon beamforming, among others. Any such technique can be used by unit 36 to solve Equation [18], and do not require sparsity assumptions. Instead, these techniques exploit the structure in the signal.

In various embodiments, unit 36 may solve the optimization problem of Equation [20] in any suitable way. Example optimization schemes that can be used for this purpose are second-order methods such as interior-point methods described by Candes and Romberg, in "l1-magic: Recovery of Sparse Signals via Convex Programming," October, 2005; and by Grant and Boyd, in "The CVX User's Guide," CVX Research, Inc., November, 2013, which are incorporated herein by reference.

Other example optimization schemes that can be used by unit 36 are first-order methods based on iterative shrinkage, as described by Beck and Teboulle, in "A Fast Iterative Shrinkage-Thresholding Algorithm for Linear Inverse Problems," SIAM Journal on Imaging Sciences, volume 2, number 1, 2009, pages 183-202; and by Hale et al., in "A Fixed-Point Continuation Method for l1-Regularized Minimization with Application to Compressed Sensing," CAAM Technical Report TR07-07, Rice University, Jul. 7, 2007, which are incorporated herein by reference.

Solving for b in an l1-norm optimization (as opposed to l0-norm optimization) provides high quality imaging, since it accounts well for both strong reflectors and speckle. Information conveyed by speckle is of high importance in many ultrasound imaging procedures. Example images that demonstrate this quality are provided in U.S. Provisional Patent Application 61/733,913, cited above.

Alternative System Implementation

FIG. 4 is a block diagram that schematically illustrates an ultrasound imaging system 90, in accordance with an alternative embodiment of the present invention. System 90 comprises an array 94 of ultrasound transducers that are used both for beamformed transmission and for beamformed reception. For the sake of clarity, the figure shows a single transmission path and a single reception path. In practice, the system comprises a respective transmission path and a respective reception path per transducer.

On transmission, a transmit beamformer 98 generates a beamformed set of digital signals for transmission. A set of Digital to Analog Converters (DACs) 102 convert the digital signals into analog ultrasound signals. A set of amplifiers 106 amplify the ultrasound signals, and the signals are fed via respective Transmit/Receive (T/R) switches 110 to array 94.

On reception, the received ultrasound signals from the transducers pass through T/R switches 110 and are amplifiers by respective amplifiers 114. A set of Low-Pass Filters (LPFs) 118 filter the received signals, and the filtered signals are sampled (digitized) using respective Analog to Digital Converters (ADCs) 122.

The digital circuitry of system 90 comprises high-speed logic that processes the digitized received signal. For each received signal, the high-speed logic comprises a Quadrature down-converter 130 followed by a pair of LPFs 134. The complex (I/Q) baseband signal produced by the down-converter is provided to a DFT module 138, which computes DFT coefficients of the received signal. A frequency-domain receive beamformer 142 recovers the beamformed signal from the DFT coefficients of the multiple received signals, using the frequency-domain beamforming methods described herein.

The system configuration of FIG. 4 is depicted purely by way of example. In alternative embodiments, any other suitable system configuration can also be used. In the present context, elements 110, 114, 118, 122, 130 and 134 serve as an input interface that receives the ultrasound reflections, and elements 138 and 142 serve as processing circuitry that computes the transducer-specific frequency-domain coefficients for each of the received signals, derives the frequency-domain coefficients of the beamformed signal from the transducer-specific frequency-domain coefficients, and reconstructs the ultrasound image of the target organ based on the beamforming frequency-domain coefficients.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
    receiving via an input interface signals from multiple respective transducers, the received signals comprising reflections of a transmitted signal from both dominant reflectors and speckle reflectors in a target;
    using processing circuitry that is coupled to the input interface, reconstructing an image of the target, by:
        computing transducer-specific frequency-domain coefficients for each of the received signals;
        deriving, from the transducer-specific frequency-domain coefficients, beamforming frequency-domain coefficients of a beamformed signal in which the reflections received from a selected direction relative to the transducers are emphasized; and
        reconstructing the image of the target at the selected direction, including reconstructing and imaging both the dominant reflectors and the speckle reflectors, based on the beamforming frequency-domain coefficients, without constraining the received signals to be sparse.

2. The method according to claim 1, wherein deriving the beamforming frequency-domain coefficients comprises computing the beamforming frequency-domain coefficients only within an effective bandwidth of the beamformed signal.

3. The method according to claim 1, wherein reconstructing the image comprises applying an inverse Fourier transform to the beamforming frequency-domain coefficients.

4. The method according to claim 1, wherein deriving the beamforming frequency-domain coefficients comprises computing the beamforming frequency-domain coefficients only within a partial sub-band within an effective bandwidth of the beamformed signal.

5. The method according to claim 1, wherein reconstructing the image comprises applying a Compressed sensing (CS) or sparse recovery process to the beamformed frequency-domain coefficients.

6. The method according to claim 1, wherein reconstructing the image comprises applying to the beamformed frequency-domain coefficients an algorithm for extracting sinusoids from a sum of sinusoids.

7. The method according to claim 1, wherein reconstructing the image comprises estimating the beamformed signal in time-domain based on the beamforming frequency-domain coefficients, and reconstructing the image from the estimated beamformed signal.

8. The method according to claim 1, wherein deriving the beamforming frequency-domain coefficients comprises computing a weighted average of the transducer-specific frequency-domain coefficients.

9. The method according to claim 8, wherein computing the weighted average comprises applying to the transducer-specific frequency-domain coefficients predefined weights that are independent of the received signals.

10. The method according to claim 1, wherein computing the transducer-specific frequency-domain coefficients comprises deriving the transducer-specific frequency-domain coefficients from sub-Nyquist samples of the received signals.

11. The method according to claim 1, wherein reconstructing the image comprises applying an l1-norm optimization to the beamforming frequency-domain coefficients.

12. The method according to claim 1, wherein reconstructing the image comprises applying a recovery process that exploits sparse structure of the received signals.

13. The method according to claim 1, wherein reconstructing the image comprises applying a recovery process that assumes the received signals are compressible but does not constrain the received signals to be sparse.

14. Apparatus, comprising:
an input interface, which is configured to receive signals from multiple respective transducers, the received signals comprising reflections of a transmitted signal from both dominant reflectors and speckle reflectors in a target; and
processing circuitry, which is configured to compute transducer-specific frequency-domain coefficients for each of the received signals, to derive, from the transducer-specific frequency-domain coefficients, beamforming frequency-domain coefficients of a beamformed signal in which the reflections received from a selected direction relative to the transducers are emphasized, and to reconstruct an image of the target at the selected direction based on the beamforming frequency-domain coefficients, including reconstructing and imaging both the dominant reflectors and the speckle reflectors, without constraining the received signals to be sparse.

15. The apparatus according to claim 14, wherein the processing circuitry is configured to compute the beamforming frequency-domain coefficients only within an effective bandwidth of the beamformed signal.

16. The apparatus according to claim 14, wherein the processing circuitry is configured to reconstruct the image by applying an inverse Fourier transform to the beamforming frequency-domain coefficients.

17. The apparatus according to claim 14, wherein the processing circuitry is configured to compute the beamforming frequency-domain coefficients only within a partial sub-band within an effective bandwidth of the beamformed signal.

18. The apparatus according to claim 14, wherein the processing circuitry is configured to reconstruct the image by applying a Compressed sensing (CS) or sparse recovery process to the beamformed frequency-domain coefficients.

19. The apparatus according to claim 14, wherein the processing circuitry is configured to reconstruct the image by applying to the beamformed frequency-domain coefficients an algorithm for extracting sinusoids from a sum of sinusoids.

20. The apparatus according to claim 14, wherein the processing circuitry is configured to estimate the beamformed signal in time-domain based on the beamforming frequency-domain coefficients, and to reconstruct the image from the estimated beamformed signal.

21. The apparatus according to claim 14, wherein the processing circuitry is configured to derive the beamforming frequency-domain coefficients by computing a weighted average of the transducer-specific frequency-domain coefficients.

22. The apparatus according to claim 21, wherein the processing circuitry is configured to compute the weighted average by applying to the transducer-specific frequency-domain coefficients predefined weights that are independent of the received signals.

23. The apparatus according to claim 14, wherein the processing circuitry is configured to derive the transducer-specific frequency-domain coefficients from sub-Nyquist samples of the received signals.

24. The apparatus according to claim 14, wherein the processing circuitry is configured to reconstruct the image by applying an l1-norm optimization to the beamforming frequency-domain coefficients.

* * * * *